United States Patent
Garnett et al.

(10) Patent No.: US 6,677,438 B1
(45) Date of Patent: Jan. 13, 2004

(54) METHOD FOR ATTACHING POLYETHYLENE GLYCOL TO MACROMOLECULES

(75) Inventors: Martin Charles Garnett, Derby (GB); Stanley Stewart Davis, Nottingham (GB); Fabio Bignotti, Brescia (IT); Paolo Ferruti, Milan (IT)

(73) Assignees: University of Nottingham, University Park (GB); Universita Degli Studi di Brescia, Brescia (IT)

( * ) Notice: Subject to any disclaimer, the term of this patent is extended or adjusted under 35 U.S.C. 154(b) by 0 days.

(21) Appl. No.: 09/462,190
(22) PCT Filed: Jul. 2, 1998
(86) PCT No.: PCT/GB98/01954
§ 371 (c)(1), (2), (4) Date: Jul. 21, 2000
(87) PCT Pub. No.: WO99/01469
PCT Pub. Date: Jan. 14, 1999

(30) Foreign Application Priority Data

Jul. 3, 1997 (GB) ............................................. 9713979

(51) Int. Cl.[7] .......................... C07K 1/00; C07K 17/08; C08H 1/00; C12N 11/08; C12N 9/96
(52) U.S. Cl. ....................... 530/402; 435/180; 435/181; 435/188; 530/815; 530/816
(58) Field of Search .................................. 435/174, 177, 435/180, 181, 188; 530/402, 815, 816

(56) References Cited

U.S. PATENT DOCUMENTS 4,179,337 A * 12/1979 Davis et al. ................. 435/181
5,550,178 A * 8/1996 Desai et al. ................... 524/56

OTHER PUBLICATIONS

Lejeune, et al., Polym. Prepr., vol. 38, No. 1, 1997 pp. 563–564.*

* cited by examiner

Primary Examiner—David M. Naff
(74) Attorney, Agent, or Firm—Oppenheimer, Wolff & Donnelly LLP

(57) ABSTRACT

A process for attaching a polyethylene glycol compound to a macromolecule to prepare a conjugate or adduct between the polyethylene glycol compound and the macromolecule is described. The process comprises the steps of (1) preparing an activated PEG or an activated PEG derivative by incorporating an acrylic ester, an acrylic thioester or an acrylamido group into the PEG or PEG derivative; (2) reacting the activated PEG or PEG derivative with a macromolecular material comprising one or more sulphydryl groups, primary amino groups and/or secondary amino groups and (3) recovering the conjugate of the PEG or PEG derivative and the macromolecular material.

48 Claims, No Drawings

METHOD FOR ATTACHING POLYETHYLENE GLYCOL TO MACROMOLECULES

FIELD OF THE INVENTION

The present invention relates to a method for attaching or bonding a polyethylene glycol (PEG) compound to a macromolecule such as a protein, a carbohydrate or other polymeric material.

BACKGROUND OF THE INVENTION

An early detailed description of the synthesis of polyethylene glycol derivatives has been given by Harris in JMS. Rev. Macromol. Chem. Phys. C25, 325, 1985.

The modification of proteins and carbohydrates by the attachment of polyethylene glycol (PEG) is known and is described, for example, by Abuchowski et al in J. Biol. Chem. 252, 3578, 1977. The process is often referred to as PEGylation.

Various coupling reactions between amino groups of proteins and carbohydrate molecules and the monomethyl ether of PEG equipped with an electrophilic functional group have also been described, see Zalipsky, Advan. Drug Del. Rev. 16, 157, 1995). The composition of the resultant graft copolymeric system is dependent on the number of available attachment sites on the starting polypeptide (or carbohydrate), the reactivity of the PEG reagent, the excess of such a reagent and the reaction conditions.

Francis et al. discloses a method of bonding polyethylene glycol to proteins and other macromolecules under very mild conditions by activation with tresyl chloride, see Biotechnol. Appl. Biochem. 12, 119, 1990.

Various methods of PEGylation are also described in U.S. Pat. No. 4,179,337, U.S. Pat. No. 4,732,863, U.S. Pat. No. 4,917,888, WO-86/04145, WO-90/04606, WO-90/06952, WO-90/13540, WO-91/01758, EP-400472, EP400486 and EP-183503.

The therapeutic value of polyethylene glycol modified proteins has also been reviewed, see Nucci et al., Advan. Drug Del. Rev. 6, 133, 1991 and Inada et al., J. Bioactive Compat. Polymer 5, 343, 1990.

SUMMARY OF THE INVENTION

We have developed a novel method of attaching a polyethylene glycol compound to suitably functionalized macromolecular materials. By a polyethylene glycol compound we include polyethylene glycol (PEG) itself and derivatives thereof (PEG derivatives) in which one or both of the terminal hydroxyl groups in the polyethylene glycol molecule has been previously modified.

DETAILED DESCRIPTION OF THE INVENTION

According to the present invention there is provided a process for attaching a polyethylene glycol compound to a macromolecule to prepare a conjugate or adduct between the polyethylene glycol compound and the macromolecule which comprises the steps of:

(1) preparing an activated PEG or an activated PEG derivative by incorporating an acrylic ester, an acrylic thioester or an acrylamido group into the PEG or PEG derivative;

(2) reacting the activated PEG or PEG derivative with a macromolecular material comprising one or more sulphydryl groups, primary amino groups and/or secondary amino groups; and (3) recovering the conjugate of the PEG or PEG derivative and the macromolecular material.

By a PEG derivative we mean a polyethylene glycol polymer in which one or both of the terminal hydroxyl groups found in polyethylene glycol itself has been modified. Examples of suitable modifications include replacing one or both hydroxyl group(s) with alternative functional groups, which may be protected or unprotected, with low molecular weight ligands, or with another macromolecule or polymer. Modification of the terminal hydroxyl groups in polyethylene glycol can be achieved by reacting the polyethylene glycol with compounds comprising complementary reactive. functional groups, i.e. functional groups which are able to undergo a reaction with the hydroxyl groups in polyethylene glycol.

Suitable PEG derivatives include compounds in which one of the terminal hydroxyl groups has been converted into a group having the formula RO— in which R is an alkyl, cycloalkyl, aryl, aralkyl or alkaryl group. Preferably R is alkyl to give a terminal alkoxy group. Preferred alkoxy groups are $C_{1-4}$ alkoxy, such as methoxy.

The macromolecular material may contain just sulphydryl, primary amino or secondary amino groups or it may contain a mixture of such groups. Suitable macromolecular materials for conjugation to a polyethylene glycol compound include therapeutic proteins such as interleukins, albumins, growth hormones, aspariginase, superoxide dismutase, monoclonal antibodies, as well as carbohydrates, such as starch and dextran. Many of these macromolecules are of biological origin. The macromolecular material may also be a polymer of biological origin which has been previously modified by a reagent to introduce a sulphydryl group or a primary or secondary amine group. A preferred macromolecular material is a protein or a poly(amino) sugar.

The preparation of a PEG or PEG derivative carrying an acrylic thioester group can be carried out using conventional techniques in which a PEG or PEG derivative containing a sulphydryl group is reacted with acryloyl chloride. The reaction is typically conducted in the presence of a base such as a tertiary amine, e.g. triethylamine, or an aqueous solution of sodium hydroxide at a temperature in the range of from 0 to 5° C. to avoid radical polymerisation between the acrylic double bonds. Suitable solvents for the reaction include aliphatic and aromatic hydrocarbons, chloroform and other halogenated hydrocarbon solvents. (See J. March, Advanced Organic Chemistry, John Wiley & Sons, New York, 3rd Edition (1985), page 362.)

The preparation of a PEG or PEG derivative carrying an acrylic ester group can be carried out using conventional techniques in which a PEG or PEG derivative containing a hydroxyl group is reacted with acryloyl chloride. The reaction is typically conducted in the presence of a base such as a tertiary amine, e.g. triethylamine, or an aqueous solution of sodium hydroxide at a temperature in the range of from 0 to 5° C. to avoid radical polymerisation between the acrylic double bonds. Suitable solvents for the reaction include aliphatic and aromatic hydrocarbons, chloroform and other halogenated hydrocarbon solvents. (See J. March, Advanced Organic Chemistry, John Wiley & Sons, New York, 3rd Edition (1985), page 346.)

The preparation of a PEG or PEG derivative carrying an acrylamido group can be carried out using conventional techniques in which a PEG or PEG derivative containing a primary or secondary amino group is reacted with acryloyl chloride. The reaction is typically conducted in the presence of a base such as a tertiary amine, e.g. triethylamine, or an aqueous solution of sodium hydroxide at a temperature in the range of from 0 to 5° C. to avoid radical polymerisation between the acrylic double bonds. Suitable solvents for the reaction include aliphatic and aromatic hydrocarbons, chloroform and other halogenated hydrocarbon solvents. (See J. March, Advanced Organic Chemistry, John Wiley & Sons, New York, 3rd Edition (1985), page 370.)

An example of such preparations is reported by Bignotti et al. (Macromol. Rapid Communic. 15, 659, 1994). Acrylating agents other than acryloyl chloride may also be used, such as 1-acryloylbenzotriazole and N-acryloyloxysuccinimide. However, acryloyl chloride is the preferred acrylating reagent.

The activated PEG or PEG derivative can be characterized by Gel Permeation Chromatography (GPC), FT-IR and UV spectroscopy. The degree of activation can be determined by end-group titration which involves adding an excess of 2-mercaptoethanol and titrating excess thiol with a calibrated $KI/I_2$ solution, or by UV spectroscopy, after calibration with a standard acrylamide or acrylic ester such as N-acryloylmorpholine or tetraethyleneglycol diacrylate, conducted at 233 nm.

Activated PEGs or activated PEG derivatives can be stored for several months at $T \leq 4°$ C. in the presence of a desiccant. A radical inhibitor such as 4-methoxyphenol may also be added to prevent radical polymerization.

The reaction of the activated PEG or activated PEG derivative with the macromolecular material is preferably performed at $pH \geq 8$, usually in the range 8<pH<9, in aqueous media. Below pH 7.5 the reaction rate tends to be slow. Alcohols or alcohol/water mixtures can also be used.

Although this step is generally conducted in the liquid phase, it is also possible to perform the reaction at the solid-liquid interface in the case of insoluble materials. When the macromolecular material is a solid, it should have sterically accessible sulphydryl, primary amine or secondary amine-groups.

Reaction temperatures in the range of from 15 to 60° C., particularly 15 to 50° C. can be used and typical reaction times are 12–48 hours. The preferred reaction temperature is between 20 and 30° C. The occurrence of vinyl radical polymerization is inhibited by conducting the reaction under an inert atmosphere, in the dark and in the presence of a radical inhibitor such as 4-methoxyphenol.

Recovery of the conjugate that is formed is generally carried out by ultrafiltration in water or by evaporating the reaction solvent and extracting the crude material with an appropriate new solvent.

The choice of procedure is mainly governed by the solubility of the adduct and the starting materials, and by their molecular weight.

The purity of the adduct can be assessed by GPC, FT-IR, NMR and UV spectroscopy. Checking for residual activated PEG or PEG derivative is usually performed spectrophotometrically at 233 nm.

When a monoalkoxy, e.g. monomethoxy, PEG derivative containing a single sulphydryl, hydroxyl or amino group is used in the above process, as is preferred, such materials may often contain a small amount, typically less than 10% by weight, of a difunctional compound having two reactive sulphydryl, hydroxyl or amino groups. These difunctional compounds can be activated at both ends with acrylic double bonds to produce a compound which is able to react twice with the macromolecular material to produce a cross-link. This can be avoided, if desired, by modifying the standard process by conducting an additional processing step (2')

between steps (2) and (3). This additional step (when employed) comprises adding a molar excess, relative to the activated alkoxy PEG derivative, of a compound which is capable of adding to residual double bonds. Typical compounds include mercaptans, such as 2-mercaptoethanol, and secondary-amines, such as morpholine. The additional step (2') is preferably performed under the same conditions as step (2), i.e. at a $pH \geq 8$, usually in the range 8<pH<9, in aqueous media at a temperature in the range of from 15 to 60° C., particularly from 15 to 50° C. and especially between 20 and 30° C. The occurrence of vinyl radical polymerization is again inhibited by conducting the reaction under an inert atmosphere, in the dark and in the presence of a radical inhibitor such as 4-methoxyphenol. Typical reaction times are 6–12 hours.

When this step is applied, residual methoxy PEG derivative is completely inactivated and cannot be re-used.

The process of the present invention has the following characteristics:

(a) Free base is the species reacting with the double bond so that the reaction rate will tend to increase as the pH is increased, i.e. as the concentration of free base is increased.

(b) No by-products are normally produced during grafting. The absence of by-product formation means that only unreacted PEG or PEG derivative needs to be separated from the conjugate during the purification stage. Furthermore, it may be possible to re-use the polyethylene glycol compound without further purification. Other PEGylation methods tend to produce toxic by-products which need to be very carefully eliminated.

(c) When the macromolecular material is a compound carrying amino groups, the aminic character of these groups tends to be unaffected by the grafting reaction. This in turn can mean that the electrical nature of the macromolecular material in water does not undergo significant changes as a consequence of grafting. In contrast, many other PEGylation processes cause complete loss of the basic character of amino groups and, therefore, a dramatic change in the electrical nature of the material.

(d) When the macromolecular material is a compound carrying primary amino groups, reaction of these groups with a double bond produces secondary amino groups which may then react with a second double bond to produce a compound comprising two PEG moieties bonded to a single amino nitrogen.

(e) Secondary amine groups tend to react more slowly than primary ones owing to steric hindrance.

The products which are produced using the process of the present invention comprise a coupling moiety or linking group that joins the macromolecular material to the polyethylene glycol compound. When a PEG or PEG derivative activated with an acrylic thioester group is employed, the following coupling moiety is present.

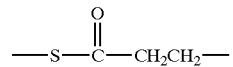

When a PEG or PEG derivative activated with the acrylic ester group is employed, the following coupling moiety is found.

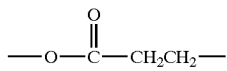

Finally, when a PEG or PEG derivative activated with an acrylamido group is employed, the following coupling moiety is found.

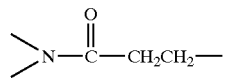

As can be seen from the above formulae, the products contain amido, ester or thioester groups which tend to make the conjugate hydrolysable resulting in the release of the starting PEG or PEG derivative. Such a process of hydrolysis could be advantageous for the biological degradation of the PEG material. It is possible to obtain conjugates with increasing stability towards hydrolysis going from thioester<ester<amido. This ability to control the stability of the linkage could be important in some medical applications.

The methoxy PEG (MPEG) derivative whose synthesis is described in Example 1, part (A), has the formula:

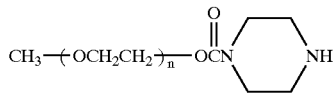

In general, MPEG derivatives having the formula:

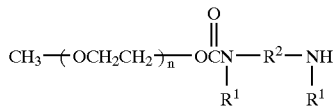

can be prepared by the same procedure as described in Example 1 using, instead of piperazine, another symmetrical bis(primary) or bis(secondary) diamine having the formula:

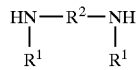

wherein $R^1$ is H or a linear or branched $C_{1-4}$ alkyl chain; and $R^2$ is a linear or branched $C_{1-4}$ alkylene chain.

Alternatively, the group

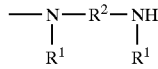

may be replaced by the group

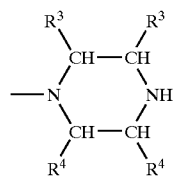

in which $R^3$ and $R^4$ are independently H or a linear or branched $C_{1-3}$ alkyl chain.

In general, a PEG derivative having the formulae $R^5$—$(OCH_2CH_2)_n$Y or the formula $R^5$—$(OCH_2CH_2)_n$X—Y, where Y is hydroxyl (OH), sulphydryl (SH), primary amino ($NH_2$) or secondary amino (NHR), X is a divalent coupling moiety or linking group whose actual structure depends on the procedure employed for preparing the PEG derivative, n is an integer, e.g. from 10 to 1000, and $R^5$ is alkyl, will be used in the process of the present invention. Preferably n is an integer of from 10 to 100 and $R^5$ is $C_{1-4}$ alkyl, especially methyl.

The key feature of the PEGylation process of the present invention is the reaction of —$NH_2$, —NHR or —SH groups on the macromolecular material with double bonds on the activated polyethylene glycol compound which are activated by the presence of electron withdrawing groups in the a position.

In principle, the PEGylation process can be applied to molecules containing a polyethylene glycol chain of any molecular weight, but, in practice, molecular weights less than 20 kilodaltons (kD) are preferred, with molecular weights in the range of from 10 to 15 kD being especially preferred.

The present invention is now illustrated, but not limited with reference to the following examples.

EXAMPLE 1

(A) Preparation of Monomethoxy-PEG Piperazinyl Formate (MPEG-PF)

Monomethoxy-PEG 1900 (12.26 g, 6.45 mmol) was dissolved in "alcohol-free" $CHCl_3$ (60 ml). The solution was dried overnight over calcium hydride, which was then removed by filtration. 1,1'-carbonyldiimidazole of 97% purity (2.16 g, 12.9 mmol) was then added and the resulting solution allowed to stand at 30° C. for 30 min after which cold water was added (10 ml) and the mixture stirred for 10 min. After separation of the phases, anhydrous piperazine (0.56 g, 12.9 mmol) was added to the organic phase and allowed to react for 20 hours at 25° C. The solution was then diluted with $CHCl_3$ (100 ml), extracted with water (5×30 ml), dried with $Na_2SO_4$, filtered, concentrated in vacuo to 60 ml and finally poured into diethyl ether at about 10° C. The powder which precipitated out was collected by filtration and dried to constant weight at 0.1 torr. The yield was 10.64 g. The GPC chromatogram exhibited one peak with retention time 1030 sec. The FT-IR spectrum showed a band in the urethane region at 1703 $cm^{-1}$. The molecular weight, determined by potentiometric titration with 0.1 M HCl, was 2190.

(B) Preparation of Monomethoxy-PEG Acrylamide (MPEG-AA)

MPEG-PF (7.07 g; 3.23 mmol) was dissolved in dry, "alcohol-free" $CHCl_3$ (10 ml) and distilled water (2 ml) was added. 2.4 ml of a 2M solution of acryloyl chloride in $CHCl_3$ (4.8 mmol) and 2.4 ml of a 2M NaOH aqueous solution (4.8 mmol) were then added together, drop-wise, under vigorous stirring while maintaining the temperature at about 5° C.

Once the addition was completed, the reaction mixture was left at 25° C. in the dark- and under stirring for 1 hour. The reaction mixture was then diluted with CHCl$_3$ to 150 ml and washed in a separatory funnel with 5% KNO$_3$ (2×30 ml) and water (1×30 ml). After drying with Na$_2$SO$_4$ and filtering, the volume was reduced to about 50 ml by evaporating most of the CHCl$_3$ in vacuo. The solution was then diluted with diethyl ether (200 ml). The product which precipitated out was collected by filtration and dried to constant weight at 0.1 torr. The yield was 6.05 g. The GPC chromatogram exhibited one peak with retention time 1020 sec. The FT-IR spectrum was very similar to that of starting MPEG-PF, but showed an amidic band at 1649 cm$^{-1}$. The molecular weight, determined spectrophotometrically at 233 nm in water using the calibration curve of N-acryloylmorpholine, was 2300.

(C) PEGylation of Human Serum Albumin (HSA)

MPEG-AA (2.07 g, 0.90 mmol), NaHCO$_3$ (50 mg, 0.60 mmol) and 4-methoxyphenol (10 mg) were added to a 20 wt. % HSA aqueous solution (5.08 g) and allowed to react at 25° C., under a nitrogen atmosphere and in the dark for 2 days. The solution was diluted and ultrafiltered in water at 10° C. through an Amicon XM50 membrane with Mw cut off 50,000 and freeze-dried. The yield was 1.21 g. The GPC chromatogram exhibited one peak with retention time 850 sec. while the retention time of native HSA was 885 sec. The UV spectrum did not show any peak near 233 nm due to residual MPEG-AA. The FT-IR spectrum presented bands of both HSA (in particular: amide I band at 1662 cm$^{-1}$ and amide II band at 1540 cm$^{-1}$) and MPEG-AA (in particular: C—O—C stretching at 1110 cm$^{-1}$). Comparison of the elemental analyses (C: 51.0%, H: 7.28%, N: 13.33%) with those of native HSA (C: 49.89%, H: 7.14%, N: 15.22%) and MPEG-AA (C: 54.49%, H: 8.87%; N: 1.25%) allowed us to estimate that the PEG content in PEGylated HSA was 15 wt. %. Therefore, the degree of PEGylation, expressed as the percentage of modified lysine residues, was about 9%. The degree of PEGylation determined by the trinitrobenzene sulphonic acid (TNBS) assay was 15%.

EXAMPLE 2

PEGylation of Human Serum Albumin (HSA)

This experiment was performed exactly as reported in Example 1, but using 4.14 g (1.80 mmol) of MPEG-AA and adding distilled water (5 ml). Yield: 1.45 g. GPC retention time: 830 sec. Degree of PEGylation, determined by the TNBS assay: 29%.

EXAMPLE 3

PEGylation of Ribonuclease A

Ribonuclease A from bovine pancreas (0.25 g), MPEG-AA (0.46 g, 0.20 mmol), NaHCO$_3$ (15 mg, 0.18 mmol) and 4-methoxyphenol (2 mg) were dissolved in distilled water (5 ml) and allowed to react at 25° C., under a nitrogen atmosphere and in the dark for 2 days. The solution was diluted and ultrafiltered in water at 10° C. through an Amicon PM10 membrane with Mw cut off 10,000 and freeze-dried. The yield was 0.28 g. The GPC chromatogram exhibited one peak with retention time 930 sec. while the retention time of native protein was 965 sec. The UV spectrum did not show any peak near 233 nm due to residual MPEG-AA. The degree of PEGylation, expressed as the percentage of modified lysine residues, was about 18%.

EXAMPLE 4

PEGylation of Ribonuclease A

This experiment was performed exactly as reported in Example 3, but using 0.92 g (0.40 mmol) of MPEG-AA. Yield: 0.45 g. GPC retention time: 910 sec. Degree of PEGylation, determined by the TNBS assay: 34%.

What is claimed is:

1. A process for attaching a polyethylene glycol (PEG) compound to a macromolecular material to prepare a conjugate or adduct between the polyethylene glycol compound and the macromolecular material which comprises the steps of:
   (1) preparing an activated PEG or an activated PEG derivative which includes carbon-carbon double bonds which are activated by the presence of electron withdrawing groups in the a position by incorporating an acrylic ester, an acrylic thioester or an acrylamido group into the PEG or PEG derivative;
   (2) reacting the activated PEG or PEG derivative with a macromolecular material comprising one or more sulphydryl groups, primary amino groups and/or secondary amino groups such that the sulphydryl groups, primary amino groups and/or secondary amino group(s) react with the carbon-carbon double bonds on the activated PEG or PEG derivative to form the conjugate or adduct; and
   (3) recovering the conjugate or adduct of the PEG or PEG derivative and the macromolecular material.

2. A process as claimed in claim 1, wherein the macromolecular material is a polymer of biological origin.

3. A process as claimed in claim 2, wherein the macromolecular material is a protein or poly(amino) sugar.

4. A process as claimed in claim 1, wherein the macromolecular material is a polymer of biological origin which has ben previously modified by a reagent to introduce a sulphydryl group or a primary or secondary amine group.

5. A process as claimed in claim 1 which is carried out at a solid/liquid interface where the macromolecular material is a solid and has a sterically accessible sulphydryl, primary amine or secondary amine group.

6. A process as claimed in any one of claims 1 to 5, wherein a PEG derivative having the formula R$^5$—(OCH$_2$CH$_2$)$_n$Y or the formula R$^5$—(OCH$_2$CH$_2$)$_n$X—Y, where Y is hydroxyl, sulphydryl, primary amino or secondary amino, X is a divalent coupling moiety, n is an integer and R$^5$ is alkyl, is used in the process.

7. A process as claimed in claim 6, wherein n is in the range of from 10 to 1000.

8. A process as claimed in claim 7, wherein n is from 10 to 100.

9. A process as claimed in claim 6, wherein R$^5$ is C$_{1-4}$ alkyl.

10. A process as claimed in claim 9, wherein R$^5$ is methyl.

11. A process as claimed in claim 6 which comprises a further step (2') conducted between steps (2) and (3) comprising adding a molar excess, relative to the activated PEG derivative, of a compound which is capable of adding to residual double bonds.

12. A process as claimed in claim 1, wherein the reaction of the activated PEG or activated PEG derivative with the macromolecular material is performed at pH≧8.

13. A process as claimed in claim 1, wherein the reaction of the activated PEG or activated PEG derivative with the macromolecular material is performed in aqueous media.

14. A process as claimed in claim 1, wherein the reaction of the activated PEG or activated PEG derivative with the macromolecular material is conducted at a temperature in the range of from 15 to 50° C.

15. A process as claimed in claim 14, wherein the reaction of the activated PEG or activated PEG derivative with the macromolecular material is conducted at a temperature between 20 to 30° C.

16. A process as claimed in claim 1, wherein the reaction of the activated PEG or activated PEG derivative with the macromolecular material is conducted under an inert atmosphere, in the dark and in the presence of a radical inhibitor.

17. A process for attaching a polyethylene glycol (PEG) compound to a macromolecular material to prepare a conjugate or adduct between the polyethylene glycol compound and the macromolecular material which comprises the steps of:
   (1) preparing an activated PEG or an activated PEG derivative which includes carbon-carbon double bonds which are activated by the presence of electron withdrawing groups in the a position by incorporating an acrylic ester, an acrylic thioester or an acrylamido group into the PEG or PEG derivative;
   (2) reacting the activated PEG or PEG derivative with a macromolecular material comprising one or more sulphydryl groups, primary amino groups and/or secondary amino groups such that the sulphydryl groups, primary amino groups and/or secondary amino groups react with the carbon-carbon double bonds on the activated PEG or PEG derivative to form the conjugate or adduct, wherein the resulting conjugate or adduct has a coupling moiety selected from the group consisting of —S—C(O)—$CH_2CH_2$— when the activated PEG or PEG derivative incorporates an acrylic thioester group, —O—C(O)—$CH_2CH_2$— when the activated PEG or PEG derivative incorporates an acrylic ester group, and —N—C(O)—$CH_2CH_2$— when the activated PEG or PEG derivative incorporates an acrylamido group; and
   (3) recovering the conjugate or adduct of the PEG or PEG derivative and the macromolecular material.

18. A process as claimed in claim 17, wherein the macromolecular material is a polymer of biological origin.

19. A process as claimed in claim 18, wherein the macromolecular material is a protein or poly(amino) sugar.

20. A process as claimed in claim 17, wherein the macromolecular material is a polymer of biological origin which has been previously modified by a reagent to introduce a sulphydryl group or a primary or secondary amine group.

21. A process as claimed in claim 17 which is carried out at a solid/liquid interface where the macromolecular material is a solid and has a sterically accessible sulphydryl, primary amine or secondary amine group.

22. A process as claimed in claim 17, wherein a PEG derivative having the formula $R^5$-(OCH$_2$CH$_2$-)$_n$Y or the formula $R^5$-(OCH$_2$CH$_2$-)$_n$X—Y, where Y is hydroxyl, sulphydryl primary amino or secondary amino, X is a divalent coupling moiety, n is an integer and $R^5$ is alkyl, is used in the process.

23. A process as claimed in claim 22, wherein n is in the range of from 10 to 1000.

24. A process as claimed in claim 23, wherein n is from 10 to 100.

25. A process as claimed in claim 22, wherein $R^5$ is $C_{1-4}$ alkyl.

26. A process as claimed in claim 25, wherein $R^5$ is methyl.

27. A process as claimed in claim 22 which comprises a further step (2') conducted between steps (2) and (3) comprising adding a molar excess, relative to the activated PEG derivative, of a compound which is capable of adding to residual double bonds.

28. A process as claimed in claim 17, wherein the reaction of the activated PEG or activated PEG derivative with the macromolecular material is performed at pH$\geq$8.

29. A process as claimed in claim 17, wherein the reaction of the activated PEG or activated PEG derivative with the macromolecular material is performed in aqueous media.

30. A process as claimed in claim 17, wherein the reaction of the activated PEG or activated PEG derivative with the macromolecular material is conducted at a temperature in the range of from 15 to 50° C.

31. A process as claimed in claims 30, whey the reaction of the activated PEG or activated PEG derivative with the macromolecular material is conducted at a temperature between 20 to 30° C.

32. A process as claimed in claim 17, wherein the reaction of the activated PEG or activated PEG derivative with the macromolecular material is conducted under an inert atmosphere, in the dark and in the presence of a radical inhibitor.

33. A process for attaching a polyethylene glycol (PEG) compound to a macromolecular material to prepare a conjugate or adduct between the polyethylene glycol compound and the macromolecular material which comprises the steps of:
   (1) preparing an activated PEG derivative wherein one of the terminal hydroxyl groups has been converted into a group having the formula RO— in which R is selected from the group consisting of alkyl, cycloalkyl, aryl, aralkyl and alkaryl and wherein the activated PEG derivative includes carbon-carbon double bonds which are activated by the presence of electron withdrawing groups in the α position by incorporating an acrylic ester, an acrylic thioester or an acrylamido group into the PEG derivative;
   (2) reacting the activated PEG derivative with a macromolecular material comprising one or more sulphydryl groups, primary amino groups and/or secondary amino groups, wherein the sulphydryl groups, primary amino groups and/or secondary amino groups react with the carbon-carbon double bonds on the activated PEG derivative to form the conjugate or adduct; and
   (3) recovering the conjugate or adduct of the PEG derivative and the macromolecular material.

34. A process as claimed in claim 33, wherein the macromolecular material is a polymer of biological origin.

35. A process as claimed in claim 34, wherein the macromolecular material is a protein or poly(amino) sugar.

36. A process as claimed in claim 33, wherein the macromolecular material is a polymer of biological origin which has been previously modified by a reagent to introduce a sulphydryl group or a primary or secondary amine group.

37. A process as claimed in claim 33 which is carried out at a solid/liquid interface where the macromolecular material is a solid and has a sterically accessible sulphydryl, primary amine or secondary amine group.

38. A process as claimed in claim 33, wherein a PEG derivative having the formula $R^5$-(OCH$_2$CH$_2$-)$_n$Y or the formula $R^5$-(OCH$_2$CH$_2$-)$_n$X—Y where Y is hydroxyl, sulphydryl, primary amino or secondary amino, X is a divalent coupling moiety, n is an integer and $R^5$ is alkyl, is used in the process.

39. A process as claimed in claim 38, wherein n is in the range of from 10 to 1000.

40. A process as claimed in claim 39, wherein n is from 10 to 100.

41. A process as claimed in claim 38, wherein $R^5$ is $C_{1-4}$ alkyl.

42. A process as claimed in claim 41, wherein $R^5$ is methyl.

43. A process as claimed in claim 38 which comprises a further step (2') conducted between steps (2) and (3) comprising adding a molar excess, relative to the activated PEG derivative, of a compound which is capable of adding to residual double bonds.

44. A process as claimed in claim 33, wherein the reaction of the activated PEG or activated PEG derivative with the macromolecular material is performed at pH≧8.

45. A process as claimed in claim 33, wherein the reaction of the activated PEG or activated PEG derivative with the macromolecular material is performed in aqueous media.

46. A process as claimed in claim 33, wherein the reaction of the activated PEG or activated PEG derivative with the macromolecular material is conducted at a temperature in the range of from 15 to 50° C.

47. A process as claimed in claim 46, wherein the reaction of the activated PEG or activated PEG derivative with the macromolecular material is conducted at a temperature between 20 to 30° C.

48. A process as claimed in claim 33, wherein the reaction of the activated PEG or activated PEG derivative with the macromolecular material is conducted under an inert atmosphere, in the dark and in the presence of a radical inhibitor.

* * * * *